(12) United States Patent
Ling

(10) Patent No.: US 10,539,532 B2
(45) Date of Patent: Jan. 21, 2020

(54) METHODS FOR TESTING NON- OR WEAKLY FERROMAGNETIC TEST OBJECTS

(71) Applicant: Basell Polyolefine GmbH, Wesseling (DE)

(72) Inventor: Antonio Ling, Huerth (DE)

(73) Assignee: Basell Polyolefine GmbH, Wesseling (DE)

( * ) Notice: Subject to any disclaimer, the term of this patent is extended or adjusted under 35 U.S.C. 154(b) by 110 days.

(21) Appl. No.: 15/743,603

(22) PCT Filed: Jul. 12, 2016

(86) PCT No.: PCT/EP2016/066472
§ 371 (c)(1),
(2) Date: Jan. 10, 2018

(87) PCT Pub. No.: WO2017/009309
PCT Pub. Date: Jan. 19, 2017

(65) Prior Publication Data
US 2018/0202971 A1 Jul. 19, 2018

(30) Foreign Application Priority Data

Jul. 13, 2015 (EP) .................................... 15176382
Feb. 1, 2016 (EP) .................................... 16153599

(51) Int. Cl.
*G01N 17/00* (2006.01)
*G01N 27/80* (2006.01)
*G01N 33/20* (2019.01)
*C10G 9/20* (2006.01)
*G01R 33/12* (2006.01)

(52) U.S. Cl.
CPC ............... *G01N 27/80* (2013.01); *C10G 9/20* (2013.01); *G01N 17/006* (2013.01); *G01N 33/20* (2013.01); *G01R 33/12* (2013.01)

(58) Field of Classification Search
CPC ...... G01N 27/80; G01N 17/006; G01N 33/20; C10G 9/20; G01R 33/12
USPC ....................................................... 73/862.68
See application file for complete search history.

(56) References Cited

U.S. PATENT DOCUMENTS

| | | |
|---|---|---|
| 3,761,804 A | 9/1973 | Steingroever |
| 4,733,178 A | 3/1988 | Koch |
| 5,006,799 A | 4/1991 | Pfanstiehl |

(Continued)

FOREIGN PATENT DOCUMENTS

| | | |
|---|---|---|
| DE | 10150762 A1 | 4/2003 |
| EP | 2207007 A1 | 7/2010 |

(Continued)

OTHER PUBLICATIONS

The International Search Report and Written Opinion for PCT/EP2016/066472 dated Sep. 9, 2016.

*Primary Examiner* — Max H Noori

(57) ABSTRACT

Methods of detecting carburization, nitriding or chromium depletion in a non- or weakly ferromagnetic test object using a permanent magnet having a magnet pull force equal to or greater than about 75N and measuring either the adhesive force to detach the magnet from the test object or the attractive force in which the magnet is being pulled towards the surface of the test object.

16 Claims, 2 Drawing Sheets

(56) References Cited

U.S. PATENT DOCUMENTS

| | | | |
|---|---|---|---|
| 5,128,613 A * | 7/1992 | Takahashi | B82Y 15/00 |
| | | | 324/225 |
| 2005/0200354 A1 | 9/2005 | Edwin et al. | |
| 2010/0170079 A1 | 7/2010 | King et al. | |
| 2010/0171493 A1 | 7/2010 | Standen | |
| 2011/0142186 A1 | 6/2011 | Gemma | |
| 2013/0033779 A1* | 2/2013 | Kodama | G11B 5/3106 |
| | | | 360/75 |
| 2015/0056427 A1* | 2/2015 | Guillemette | C25D 5/34 |
| | | | 428/209 |
| 2017/0271556 A1* | 9/2017 | Yoon | H01L 33/22 |

FOREIGN PATENT DOCUMENTS

| | | |
|---|---|---|
| GB | 1562444 A | 3/1980 |
| WO | WO-2004023133 A1 | 3/2004 |
| WO | WO-2009138503 A1 | 11/2009 |

* cited by examiner

METHODS FOR TESTING NON- OR WEAKLY FERROMAGNETIC TEST OBJECTS This application is the U.S. National Phase of PCT International Application PCT/EP2016/066472, filed Jul. 12, 2016, claiming benefit of priority to European Patent Application No. 15176382.8, filed Jul. 13, 2015, and European Patent Application No. 16153599.2, filed Feb. 1, 2016, the disclosures of which are incorporated herein by reference in their entirety.

FIELD

In general, the present disclosure relates to the field of chemistry. More specifically, the present disclosure relates to analytical chemistry. In particular, the present disclosure relates to methods of detecting carburization, nitriding, or chromium depletion in non- or weakly ferromagnetic test objects.

BACKGROUND

To cleave hydrocarbons, a stream of hydrocarbon is passed through a cracking tube or coil and thermally cracked at high temperatures and pressures within the coils. The coils can be made of high-alloy austenitic (including Fe—Ni—Cr alloy) stainless steel pipes joined through welding. In some instances, a CrNi weld material can be used.

Despite being made of high quality alloy austenitic steel, the coils can undergo progressive embrittlement or corrosion from the inside and on the outside. On the outside, the exterior of the coils can come into contact with heating gas (including natural gas or high methane natural gas) used in the cracking furnace as well as gaseous combustion products contained in the exhaust stream (including $CO_2$, CO, and $NO_x$). It is believed that such gases can diffuse into the coils because of the high surface temperatures and allow for the formation of nitrides and carbo-nitrides, thereby causing embrittlement of the coil material and reduce the lifespan of the coils. In some instances, from the inside and because of thermal stress on the coil material, carbon atoms can diffuse via the wetted interior surface of the coils into the coil material, thereby contributing to embrittlement of coil material. In some instances, coil materials are damaged during operation by carburizing, nitriding, internal oxidation, depletion of chromium, and stress cracking due to longitudinal elongation.

Under the influence of high temperatures and pressures, such corrosion or embrittlement can lead to cracks or tears in the coil walls, which in turn, can lead to coil rupture and failure of the cracking furnace.

To prevent coil ruptures or furnace failures, the coils can be replaced at regular intervals. However due to the high costs involved in replacing a coil in a cracking furnace, an ideal time for replacing a coil is when the corrosion or embrittlement of the coil material has reached a state that the coil is considered to have reached "end of life". For this reason, coils are inspected at regular intervals. Notably, metallurgical and destructive testing require dismantling coils and thus are not appropriate for inspecting coils in situ. Non-destructive visual inspections including dimension analyses of the coil (including, for example. determination of changes in dimensions or form), while helpful in detecting certain potential failure indicators, the visual inspections do not allow for recognition of damage due to chromium depletion, nitriding, or carburizing.

SUMMARY OF THE INVENTION

In a general embodiment, the present disclosure provides a method of detecting carburization, nitriding or chromium depletion in a non- or weakly ferromagnetic test object, including the steps: a) applying a permanent magnet having a magnet pull force equal to or greater than about 75N to a surface of a non- or weakly ferromagnetic test object; and b) measuring the adhesive force to detach the magnet from the test object.

In a general embodiment, the present disclosure provides a method of detecting carburization, nitriding or chromium depletion in a non- or weakly ferromagnetic test object, including the steps: a) positioning a permanent magnet having a magnet pull force equal to or greater than about 75N at a fixed distance from a surface of a non- or weakly ferromagnetic test object, wherein the surface of the magnet facing towards the surface of the test object is the working surface of the magnet and wherein the working surface of the magnet is not in direct or indirect contact with the surface of the test object; and b) measuring the attractive force in which the magnet is being pulled towards the surface of the test object.

In some embodiments, the non- or weakly ferromagnetic test objects are made from or contain austenitic stainless steel, alternatively, the test objects are conduits made from or containing austenitic stainless steel, alternatively, the test objects are a furnace coil or a part of furnace coil made from or containing austenitic stainless steel. In some embodiments, the test object is a cracking coil or a part of cracking coil. In a general embodiment, the present disclosure provides a system for measuring magnet force made from or containing a permanent magnet having a magnet pull force equal to or greater than about 75N, wherein the magnet is attached to a hand-held electronic force measurement device via a bracket which includes two wheels or rollers.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

BRIEF DESCRIPTION OF FIGURES

The following figures illustrate preferred embodiments of the subject matter disclosed herein. The claimed subject matter may be understood by reference to the following description taken in conjunction with the accompanying figures, in which like reference numerals identify like elements, and in which:

DETAILED DESCRIPTION

Figure 1:
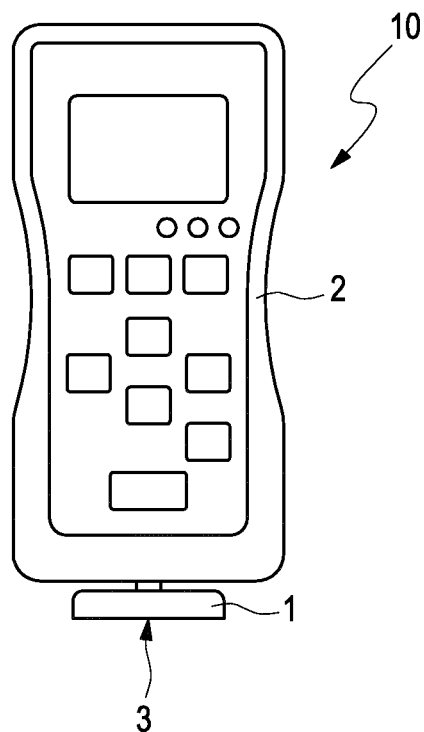
FIG. 1 shows a front view of a system for use in measuring adhesive force.

In a general embodiment, the present disclosure provides a method of detecting carburization, nitriding or chromium depletion in a non- or weakly ferromagnetic test object, including the steps: a) applying a permanent magnet having a magnet pull force equal to or greater than about 75N to a surface of a non- or weakly ferromagnetic test object; and b) measuring the adhesive force to detach the magnet from the test object. In some embodiments, the non- or weakly ferromagnetic test object is made from or contains austenitic stainless steel.

In the present description, the term "working surface of the magnet" refers to the surface of the magnet facing towards the surface of the test object. In some embodiments, the working surface is planar.

In the present description, the term "adhesive force" refers to the minimum force to pull a strong permanent magnet off a test object. In the present description, the term "attractive force" refers to the strength of the pull of a strong permanent magnet towards a test object. In some embodiments, the step of measuring the adhesive force further includes applying a gradually increasing force such that the magnet is being pulled away from the surface of the test object, the adhesive force being applied in a direction perpendicular to the working surface of the magnetic and through the center of force of the magnet and continuing application of the adhesive force until the magnet detaches from the surface of test object.

For symmetrical magnets, the center of force coincides with the magnet's center of gravity. For non-symmetrical magnets, the center of force can be identified by testing.

In some embodiments, the applied force to detach the magnet may be applied manually, pneumatically, hydraulically, or electromechanically. In some embodiments, the force may be applied onto the magnet or onto the test object, where then the test object or magnet, respectively, is immobile. In some embodiments of testing coils in a furnace, the applied force to detach the magnet is applied to the magnet because the coils are fixed in position within the furnace.

For test objects which are purely non-ferromagnetic, the working surface of the magnet will not adhere to the surface of the test object. For such cases, the measure of force to detach the magnet from the test object (adhesive force) can be defined as zero. For purposes of this disclosure, non- or weakly ferromagnetic test objects in their original state exhibit a measured adhesive force less than one Newton relative to a magnet working surface area of 4.335 cm$^2$ (that is, less than 2.3 mPa in terms of the measured force per area). Without being bound to a particular theory, applicants believe that a non-magnetic austenitic structure or phase is converted to a ferromagnetic structure or phase following depletion of chromium from the formerly non-magnetic austenite steel object or dissolution of carbon or nitrogen reaching a particular level in the formerly non-magnetic austenite steel object. The converted regions of the formerly non-magnetic austenite steel object then exhibits ferromagnetism. As such, the applicants believe that corrosion or embrittlement processes are associated with the generation of ferromagnetic regions within austenitic steel. For such objects containing regions of higher ferromagnetism due to the damaging effects of carburization, nitriding or chromium depletion, the measured adhesive force will be higher and proportional to the magnitude of ferromagnetic content in the object. The methods described herein relate to structural changes within the test objects, not to modification on the surface or within surface layers of the test objects. Moreover, the applicants have found that a magnet having a magnet pull or breakaway force equal to or greater than about 75 N responds to levels of ferromagnetism correlating to the presence or the extent of damage from corrosion or embrittlement processes.

In some embodiments and with regard to measuring adhesive force, the working surface of the magnet is placed directly in contact with the surface of the test object. In some embodiments, non-magnetic spacers may be used between the working surface of the magnet and the surface of the test object to create a "gap" or "air-gap" between the two named surfaces, thereby providing a sandwich configuration. The sandwich configuration of test object/spacer(s)/magnet results in the working surface having indirect contact with the test object surface through the intermediate spacer(s). Because the magnet is adhered to the test object through the intermediate non-magnetic spacer(s), the force to detach the indirectly-adhered magnet will be lower than the force to detach the directly-adhered magnet. In some embodiments and to detect relatively small amounts or regions of ferromagnetism in a non- or weakly ferromagnetic test object, the use of non-magnetic spacers is avoided and the working surface of the magnet is in direct contact with the test object surface.

In the present description, the protective layer having a thickness of 50 micron or less, which can be found on the outer surfaces of commercial magnets, is not considered a spacer. In some embodiments, the protective layer is a result of nickel plating or an epoxy resin coating or a combination thereof. The exclusion of the protective layer as a spacer notes that (i) the magnet pull force of a magnet is given in terms of the magnet as supplied with its protective plating or coating and (ii) the exterior surface of the plated or coated magnet on the working end of the magnet is deemed as the working surface. In regard to the attractive force measurements, the distance between the working surface of the magnet and the test object surface is the specified distance.

In a general embodiment, the present disclosure provides a method of detecting carburization, nitriding or chromium depletion in a non- or weakly ferromagnetic test object, including the steps: a) positioning a permanent magnet having a magnet pull force equal to or greater than about 75N at a fixed distance from a surface of a non- or weakly ferromagnetic test object, wherein the working surface of the magnet is not in direct or indirect contact with the surface of the test object; and b) measuring the attractive force in which the magnet is being pulled towards the surface of the test object. In some embodiments, there is a free or unoccupied gap between the working surface of the magnet and the surface of the test object. In the general embodiment, the attractive force is measured in the absence of an applied force. In some embodiments, this method is used in-situ or under tight spatial constraints.

In some embodiments, a non-magnetic spacer may be used between the working surface of the magnet and the test object surface, providing that the working surface of the magnet is not in direct or indirect contact with the test object surface, that is, there is a free and an unoccupied gap between the surfaces. In some embodiments and to detect relatively small amounts or regions of ferromagnetism in a non- or weakly ferromagnetic test object, the use of non-magnetic spacers is avoided.

In some embodiments, the working surface of the magnet and the surface of the test object are located in close proximity for the purposes of easing performance and facilitating detection of minimal levels of ferromagnetism. In some embodiments, the fixed distance between the working surface of the magnet and the surface of the test object is in the range from about 0.05 mm up to and including about 6 mm. In some embodiments, the distance is equal to or less than about 4.5 mm, alternatively equal to or less than about 3 mm, alternatively, equal to or less than about 2 mm. In some embodiments, the distance is equal to or greater than about 0.075 mm, alternatively equal to or greater than about 0.1 mm, alternatively equal to or greater than about 0.5 mm. In some embodiments, when the form of the test object surface or the working surface of the magnet, the height of the free gap between two surfaces is not equidistant over the area of the two surfaces, the height of the smallest gap between the two surfaces is designated the fixed distance.

In some embodiments, the attractive force is measured in a direction perpendicular to the working surface of the magnet and through the center of force of the magnet. For symmetrical magnets, the center of force coincides with its center of gravity; for non-symmetrical magnets, the center of force can be determined by testing.

In some embodiments, the attractive force is measured statically. In some embodiments, the attractive force is measured at a single location or position on the test object. In some embodiments, the attractive force is measured dynamically. In some embodiments, the magnet is displaced over the surface of the test object while maintaining a fixed distance and measuring the attractive force. In some embodiments, dynamic measurement allows for an easy and rapid scan over a portion of a larger test object, such as along a length of a coil in a cracking furnace. In some embodiments, the velocity by which the magnet is moved over the surface of the test object is in the range from about 1 mm/s to about 300 mm/s, alternatively from about 10 mm/s to about 100 mm/s, alternatively from about 30 mm/s to about 50 mm/s.

Figure 3:
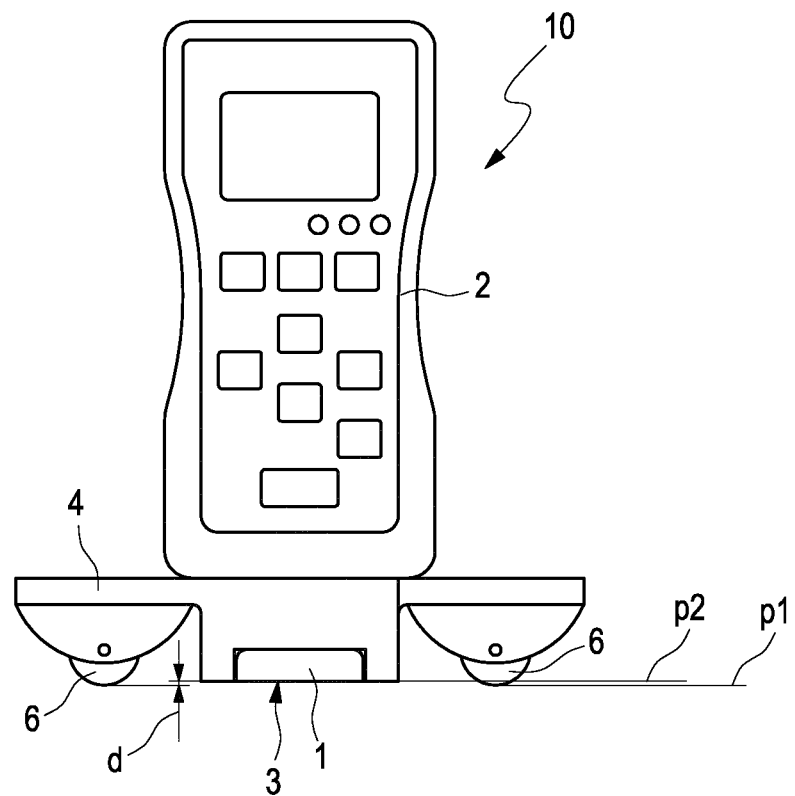
FIG. 3a shows a front view of a system for use in measuring attractive force.
FIG. 3b shows a plane view of the system shown in FIG. 3a, showing the working surface of the magnet.
Figure 3:
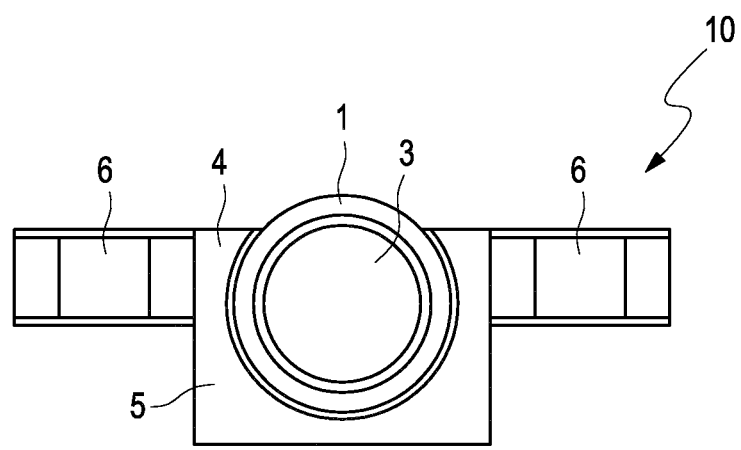

In some embodiments for measuring attractive force dynamically, the magnet is attached to a hand-held electronic force measurement device via a bracket which includes wheels or rollers. In some embodiments, the bracket has two or more wheels or rollers arranged to lie on a straight line. In some embodiments, the bracket has two wheels or rollers. In some embodiments, the most exterior surfaces of the wheels define a plane (p1) and the working surface of the magnet defines a second plane (p2) where the two planes are parallel or about parallel and spaced apart having a distance in the range from about 0.05 mm up to and including about 6 mm. In some embodiments, the distance is equal to or less than about 4.5 mm, alternatively equal to or less than about 3 mm, alternatively, equal to or less than about 2 mm. In some embodiments, the distance is equal to or greater than about 0.075 mm, alternatively equal to or greater than about 0.1 mm, alternatively, equal to or greater than about 0.5 mm. An embodiment of a system for dynamically measuring attractive force is shown in FIG. 3.

In a general embodiment, the present disclosure provides a system for measuring magnet force made from or containing a permanent magnet having a magnet pull force equal to or greater than about 75N, wherein the magnet is attached to a hand-held electronic force measurement device via a bracket which includes two wheels or rollers.

In some embodiments, magnet pull force of permanent magnets is determined by the Magnet Distributors and Fabricators Association (MDFA) Standard published under the designation "MDFA Pull Test Standard, Standard MDFA 101 95, Test Method for Determining Breakaway Force of a Magnet", incorporated herein by reference in its entirety; the method being carried out at 23° C., without an optional spacer and using a mild steel test plate made of 1018 cold rolled steel (see ASTM A794) and having a surface roughness of 63±5 micro-inches (1.60±0.13 micrometer), flatness within 0.001 inch (25.4 micrometer) over the contact surface area and a thickness such that the plate remains unsaturated by the magnetic flux of the magnet being tested (that is, a measured flux density on the surface of the plate opposite to the surface with which the magnet is in contact, is less than 5 Gauss). ASTM A794 is entitled "Standard Specification for Commercial Steel (CS), Sheet, Carbon (01.6% Maximum to 0.25% Maximum), Cold-Rolled." The term "ASTM D 256" as used herein refers to a specification that covers standard requirements for cold-rolled commercial steel sheet coils and cut lengths, which Specification is incorporated herein by reference in its entirety.

In some embodiments, the permanent magnets have a magnet pull force equal to or greater than about 90N, for purposes of easing performance and facilitating detection of ferromagnetism. In some embodiments, the magnet pull force is equal to or greater than about 110N, alternatively equal to or greater than about 125N, alternatively equal to or greater than about 150N. In some embodiments, permanent magnets having a magnet pull force of about 1000 N or even higher may be used. In some embodiments, permanent magnets have a magnet pull force equal to or less than about 750N, alternatively equal to or less than about 600 N, alternatively equal to or less than about 500N.

In some embodiments, the permanent magnets are rare earth magnets. In some embodiments, the rare earth magnets are samarium or neodymium-containing magnets. In some embodiments, the rare earth magnets are samarium cobalt alloy magnets or neodymium, iron and boron alloy magnets. In some embodiments, the rare earth magnets are used for compactness and use in tight spatial constraints.

In some embodiments, the size of the magnet is such that the magnet does not extend beyond the outer boundaries of the test object, during measurement. In some embodiments, the surface area of working surface of the magnet is selected such that when the magnet is placed against the surface of the test object, the complete surface area of the working surface of the magnet can make contact to or faces towards the test object being measured.

In some embodiments and in regard to planar test objects or test objects having a portion or portions that are about planar, the surface area of working surface of the magnet is selected such that when the magnet is placed against the surface of the test object, the magnet can make contact over the complete surface area of its working surface to the test object being measured. Accordingly, when the magnet is positioned at a fixed distance from the test object surface, the working surface of the magnet over its complete surface area is equidistant or about equidistant to the surface of the test object.

In some embodiments and in regard to non-planar test objects, the surface area of working surface of the magnet is such that when the magnet is placed against the surface of the test object, (a) the magnet can make contact over a portion of the surface area of its working surface to the surface of the test object being measured and (b) the remaining portion of the surface area of the magnet working remains spaced apart from the surface of the test object at a distance of no greater than about 1.5 mm, alternatively no greater than about 0.75 mm, alternatively no greater than about 0.5 mm. In some embodiments, the test surface has a form that is concave or convex relative to a cross-section of the test object. In some embodiments, when a magnet having a planar working surface is placed onto the exterior surface of a tubular test object for an adhesive force measurement, (a) at least a central portion of the magnet working surface will be in direct contact with the test object surface and (b) the remaining portions of magnet working surface will be spaced apart from the test object surface at height of about 1.5 mm, alternatively about 0.75 mm, alternatively about 0.5 mm, alternatively lower, alternatively to about zero. In some embodiments, the tubular test object is a furnace coil such as a cracking coil. In some embodiments, when the height of the free gap between magnet and test object surfaces is not equidistant, the smallest gap between the two surfaces is designated the fixed distance. In some embodiments, when a magnet having a planar working surface is positioned at a fixed distance from the exterior surface of a tubular test object, the height of the gap between the test object surface and the magnet working surface at the center of the magnet ("gap-height-at-center") represents the smallest gap and thus the fixed distance. In some further embodiments, the height of the gap between the test object surface and the remaining portions of magnet working surface is equal to the gap-height-at-center up to a value corresponding to the gap-height-at-center plus about 1.5 mm, alternatively plus about 0.75 mm, alternatively plus about 0.5 mm. In some embodiments, the working surface of the magnet is applied to or positioned relative to the non-planar surface of the test object such that the adhesive or attractive force is being measured during the testing.

In some embodiments, the test objects are curved coils in cracking furnace having an outer diameter in the range from about 70 to about 300 mm and the magnets have working surfaces with surface area equal to or less than about 10,000 $mm^2$, alternatively equal to or less than about 8,000 $mm^2$, alternatively equal to or less than about 5,000 $mm^2$, alternatively equal to or less than about 3,000 $mm^2$. In some embodiments, the magnets have working surface areas of about 3 $mm^2$ or less. In some embodiments, the magnets have a working surface area of at least about 35 $mm^2$ or greater. In some embodiments, the magnet has a working surface area as large as possible based upon the form and the dimension of the test surface or the spatial configuration of the system or environment where the measurements are to be performed.

In a general embodiment, the present disclosure provides a method of monitoring the conditions of cracking coils in a furnace including repeatedly detecting on the cracking coils located in situ in the furnace carburization, nitriding or chromium depletion by a method including the steps: a) applying a permanent magnet having a magnet pull force equal to or greater than about 75N to a surface of the cracking coil and b) measuring the force to detach the magnet from the cracking coil. In some embodiments, the method includes the steps: a) positioning a permanent magnet having a magnet pull force equal to or greater than about 75N at a fixed distance from a surface of the cracking coil, wherein the surface of the magnet facing towards the surface of the cracking coil is the working surface of the magnet and wherein the working surface of the magnet is not in direct or indirect contact with the surface of the cracking coil and b) measuring the attractive force in which the magnet is being pulled towards the surface of the cracking coil. In some embodiments, repeated measurements are started before start-up of the cracking coils. In some embodiments, the measurements are carried out in time intervals of from about 1 to about 3 years, alternatively from about 1 to about 2 years, alternatively about 1 year. In some embodiments, these measurements are repeated over the whole lifetime of the cracking coils.

In some embodiments, the repeatedly measuring of the extent of magnetization and the extent of corrosion and/or embrittlement of the cracking coils are used to develop trend analyses of a coil over its lifetime, thereby facilitating assessment of whether a coil should be replaced. In some embodiments, the long-term data collection regarding cracking coils in situ is used to understand corrosion/embrittlement trends within a cracking furnace. In some embodiments, the data is collected over the whole lifetime of the cracking coils.

In some embodiments, the non- or weakly ferromagnetic test objects are made from or contain austenitic stainless steel, alternatively, the test objects are conduits made from or containing austenitic stainless steel, alternatively, the test objects are a furnace coil or a part of furnace coil made from or containing an austenitic stainless steel. In some embodiments, the test object is a cracking coil or a part of cracking coil.

Examples

Adhesive Force Measurement

The following method is used to measure the adhesive force to detach a magnet from a surface of a test object. The magnet has a magnet pull force and a working surface area.

The magnet has a surface roughness (Ra) of about 1.60 micrometer or less and a flatness within about 25.4 micrometer over its working surface.

When the surface area of the (a) test object is planar or (b) a portion or portions of the test object are about planar and the magnet is placed against the surface of the test object, the area of the working surface is such that (i) the complete surface area of the working surface of the magnet can make contact to or faces towards the test object being measured and (ii) the magnet can make contact over the complete surface area of its working surface to the surface of the test object being measured. When the surface of the test object is non-planar and the magnet is placed against the surface of the test object, the surface area of working surface of the magnet is such that (i) the magnet can make contact over a portion of the surface area of its working surface to the test object being measured and (ii) the remaining portion of the surface area of the magnet working is spaced apart from the test object at a distance no greater than about 1.5 mm, alternatively no greater than about 0.75 mm, alternatively no greater than about 0.5 mm. For a non-planar test object, the magnet is applied to the surface of the test object so that the plane defined by the working surface of the magnet is parallel to a plane tangent to the test object surface at a point directly opposite to the center point of the magnet working surface.

A device for measuring the adhesive force to pull the magnet away from the surface of the test object is coupled with a method or a device for gradually increasing the force, whereby the force applied is perpendicular to the plane of the working surface of the magnet and through the center of force of the magnet. Depending on the particular configuration and measurement set-up, the applied force may be a pulling force or a pushing force as long as the force evokes a pulling away of the magnet from the surface of the test object.

A non-magnetic spacer may be used.

The test is performed at 23° C. according to the following:

1. The working surface of the magnet is placed flat against the surface of the test object. If a non-magnetic spacer is being used, the spacer is placed between the magnet and test object.

If the magnet does not adhere to the test object, non-adherence is recorded and the testing is complete. The adhesive force value is denoted as "zero" Newton.

2. Attach the magnet to the measurement apparatus being used to measure adhesive force. Step 2 may be performed prior to step 1.

3. Adjust the force-measuring device to zero after the set up is complete and prior to applying a force.

4. Apply a gradually increasing force to separate the magnet from the surface of the test object. Continue increasing the force until the magnet detaches from the test object surface.

5. Record the value at which the magnet detaches from the test object surface.

6. Repeat testing until three readings have been obtained which are within 10% of each other. Calculate the average of these results and use this value as the adhesive force.

7. Report adhesive force, magnet pull force, and surface area of magnet working surface. If the surface of the test object is non-planar, indicate that the test object is non-planar and the general dimensions regarding the magnet working surface and the test object surface. For the magnet, general dimensions can include circular and diameter. For the test object, general dimensions can include tubular and diameter. If applicable, report the use of a spacer and its thickness. The report can include the type and grade of magnet material as well as the presence and type of protective layer.

Attractive Force Measurement

The following method is used to measure the attractive force of a magnet towards a surface of a test object. The magnet has a magnet pull force and a working surface area. The working surface of magnet is positioned at a fixed distance to the surface of the test object.

The magnet has a surface roughness (Ra) of about 1.60 micrometer or less and a flatness within about 25.4 micrometer over its working surface.

When the surface area of the (a) test object is planar or (b) a portion or portions of the test object are about planar and the magnet is placed against the surface of the test object, the area of the working surface is such that (i) the complete surface area of the working surface of the magnet can make contact to or faces towards the test object being measured and (ii) the magnet can make contact over the complete surface area of its working surface to the surface of the test object being measured. During the test, the working surface is equidistant to the surface of the test object. When the surface of the test object is non-planar and the magnet is placed against the surface of the test object, the surface area of working surface of the magnet is such that (i) the magnet can make contact over a portion of the surface area of its working surface to the test object being measured and (ii) the remaining portion of the surface area of the magnet working is spaced apart from the test object at a distance no greater than about 1.5 mm, alternatively no greater than about 0.75 mm, alternatively no greater than about 0.5 mm ("secondary distance"). The free gap between the working surface and test object surface with the smallest height corresponds to a specified distance and the largest gap height is no greater than the sum of the specified distance and the secondary distance. For a non-planar test object, the magnet is applied to the surface of the test object so that the plane defined by the working surface of the magnet is parallel to a plane tangent to the test object surface at a point directly opposite to the center point of the magnet working surface.

A device for measuring the attractive force of pulling the magnet towards the test object surface is coupled with a method or a device for positioning the working surface of the magnet at a fixed distance from test object surface and in an orientation such that (i) the attractive force in a direction perpendicular to the surface of the test object and through the center of force of the magnet is being measured and (ii) the working surface of the magnetic is not in direct or indirect contact with the surface of the test object.

A non-magnetic spacer may be used at a location between the working surface of the magnet and test object surface, provided the working surface of the magnet is not in direct or indirect contact with the test object surface.

The test is performed at 23° C. according to the following:

1. The working surface of the magnet is positioned at a fixed distance to the surface of the test object. The working surface of the magnet is not in direct or indirect contact with the surface of the test object. Alternatively, a non-magnetic spacer is placed between the magnet and test object while the magnet working surface and the test object surface are not in direct or indirect contact with one another.

2. Attach the magnet to the measurement apparatus being used to measure attractive force. Step 2 may be performed prior to step 1.

3. Re-set the force-measuring device to zero after set up is complete.

4. Measuring the attractive (pulling) force of the magnet towards the surface of the test object and record the value.

5. Repeat steps 3 and 4 until three readings have been obtained that are within 10% of each. Calculate the average of these results and use this value as the attractive force.

6. Report attractive force, magnet pull force, surface area of magnet working surface and specified distance. If the surface of the test object is non-planar, indicate that the test object is non-planar and the general dimensions regarding the magnet working surface and the test object surface. For the magnet, general dimensions can include circular and diameter. For the test object, general dimensions can include tubular and diameter thereof. If applicable, report the use of a spacer and its thickness as well as unoccupied gap height and its position. The report can include the type and grade of magnet material as well as the presence and type of protective layer.

Exemplary Measurements of Cracking Coils

In the following examples, the coils measured were 100 mm in diameter and prepared from the following austenitic steel based materials:

- "GX45NiCrSiNbTi35-25"—a cast austenitic steel with 35% nickel, 25% chromium plus niobium, titanium and other components marketed by Schmidt+Clemens GmbH under the trade designation CENTRALLOY G 4852 Micro R;
- "GX45NiCrSiNbTi45-35"— an air melted nickel-base alloy consisting of a nickel-chromium-iron-silicon matrix with high chromium level and rare earth additions marketed by Schmidt+Clemens GmbH under the trade designation CENTRALLOY ET 45 Micro; and
- "GX10NiCrNb32-20"—an air melted iron-base alloy having low carbon and niobium content with an austenitic iron-chromium-nickel matrix marketed by Schmidt+Clemens GmbH under the trade designation CENTRALLOY G 4859.

A sintered NdFeB N35 pot magnet having a nickel-plated surface having an outer diameter of 32 mm, height 8 mm, and measured inner magnet-core diameter of 23.5 mm (surface area 433.5 mm$^2$=0.0004335 m$^2$) as supplied by BR Technik Kontor under designation BMI 32-6 was used. The magnet pull force was measured and determined to be 25 kg (245.25 N). The sintered neodymium magnet grade N35 exhibits the following magnetic characteristics: remanence or residual induction (Br) 1.17 to 1.25 Tesla, coercivity $(H_{cB}) \geq 860$ to 955 kA/m; intrinsic coercivity $(H_{cJ}) \geq 955$ kA/m; maximum energy product $(BH_{max})$ 263 to 302 kJ/m³.

A system (10) for measuring adhesive force is illustrated in FIG. 1. The pot magnet (1) was attached to a hand-held electronic force measurement device (2) marketed by Sauter GmbH under the designation "FL", so that during the measurements, the tension force exerted was in a direction perpendicular to the working surface (3; not visible) of the magnet and through the center of force of the magnet. For the reported coil testing, the working surface of the magnet was placed on the exterior surface of the coil being tested. After the measurement device was re-set to zero, the system was pulled manually away from cracking coil, whereby the force upon detachment of the magnet from the coil was measured and recorded.

Figure 2:
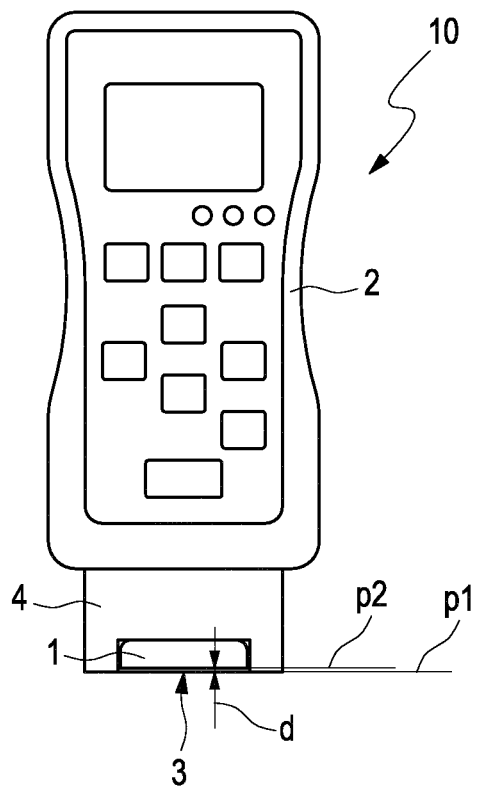
FIG. 2a shows a front view of a system for use in measuring attractive force.
FIG. 2b shows a perspective view of a system shown in FIG. 2a, showing the working surface of the magnet.
Figure 2:
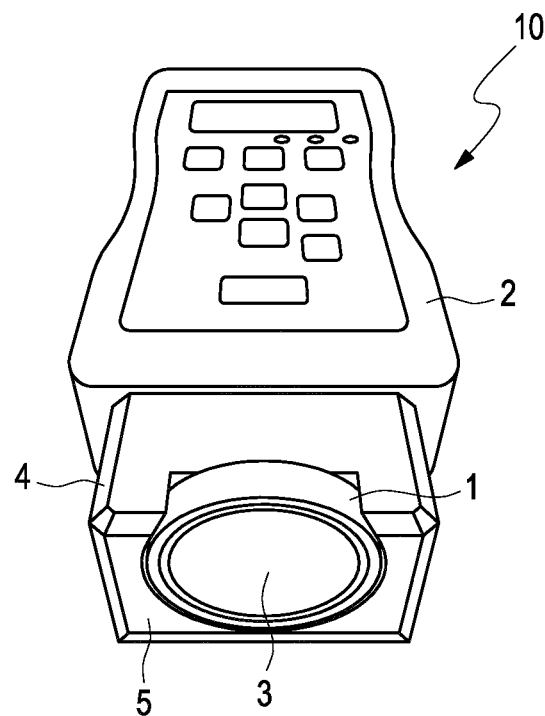

A system (10) for static measurement of attractive force is illustrated in FIG. 2 showing a front view (FIG. 2a) and a perspective view towards the bottom (FIG. 2b). The pot magnet (1) was attached to a hand-held electronic force measurement device (2) in conjunction with a bracket (4) having a mounting base (5). The magnet was attached to the measurement device such that the attractive force in a direction perpendicular to the working surface (3) of the magnet and through the center of force of the magnet was measured. The most exterior surface of the mounting base defines a plane (p1) and the working surface (3) of the magnet defines a second plane (p2), where the two planes are parallel or about parallel and spaced apart—the height of the space defining a specified fixed distance (d). The height of the space, and thus the specified distance, was 1 mm. For the reported coil testing, the bracket was oriented with its long axis along the length of the cracking coil being tested and the mounting base thereof placed on the exterior surface of the coil being tested so that 1 mm free gap was provided between the working surface of the magnet and test coil surface. After the measurement device was re-set to zero, the measurement device measured the attractive force as the magnet was attractively pulled towards the surface of the test coil.

A system (10) for dynamic measurement of attractive fore is illustrated in FIG. 3 showing a front view (FIG. 3a) and a perspective view towards the bottom (FIG. 3b). The pot magnet (1) was attached via a bracket (4) to a hand-held electronic force measurement device (2) so that the attractive force in a direction perpendicular to the working surface (3) of the magnet and through the center of force of the magnet was measured. The bracket included two wheels or rollers (6). The most exterior surfaces of the wheels define a plane (p1) and the working surface (3) of the magnet defines a second plane (p2) where the two planes are parallel or about parallel and spaced apart—the height of the space defining a specified fixed distance (d). The height of the space, and thus the specified distance, was 1 mm. For the reported coil testing, the bracket was oriented with its long axis along the length of the cracking coil being tested and the wheels of the bracket were placed against the exterior surface of the coil so that 1 mm free gap was provided between the working surface of the magnet and test coil surface. After the measurement device was re-set to zero and while maintaining the specified fee gap, the system was manually rolled along a length of the coil and the measuring device measured the attractive force as the magnet was attractively pulled towards the test coil.

Adhesive Force Measurements:

The results of adhesive force measurements on cracking coils made of GX45NiCrSiNbTi35-25, which coils were located in a cracking furnace at positions at which the coils were heated from below, are shown in Table 1. The measurements were carried out with a magnet having a working surface of 434 mm² on groups of coils which have been used in the cracking furnace for about the same time. Further measurements were conducted on coils which had been replaced from such furnace. Table 2 reports measurements on cracking coils made of GX55CrNiSiNbTi30-30.

TABLE 1

Measurement of coils made of GX45NiCrSiNbTi35-25 in a cracking furnace heated from below and such coils replaced from such cracking furnace

| Number of Coils | Age at time of measure | Measured Force (N) | Measured Force per area (mPa) |
|---|---|---|---|
| 16 coils | 0 | <1 | <2.3 |
| 94 coils | 6 years ± 2 month | 1-4 | 2.3-9.2 |
| 96 coils* | 7 years ± 1 month | 2-5 plus a single 11 | 4.6-11.5 plus 25.3 |
| 96 coils | 10 years ± 1 month | 1-4 | 2.3-9.2 |
| 48 coils | deemed damaged and replaced (age at time of coil replacement: 3 years + 2 month | 17-31 | 39.1-71.3 |

*coils located in critical region of furnace

TABLE 2

Measurement of coils made of GX55CrNiSiNbTi30-30 in a cracking furnace heated from below and such coils replaced from such cracking furnace

| Number of Coils | Age at time of measure | Measured Force (N) | Measured Force per area (mPa) |
|---|---|---|---|
| 10 coils | 0 | <1 | <2.3 |
| 53 coils | 3 years ± 2 months | <1-16 | <2.3-36.8 |
| 5 coils | deemed damaged and replaced (age at time of coil replacement: 3 years + 2 month | 17-21 | 39.1-48.3 |

Attractive Force Measurements:

The results of attractive force measurements on cracking coils made of diverse austenitic steels, which coils were located in a cracking furnace at positions at which the coils were heated from the side and below, are shown in Table 3. The measurements were carried out with a magnet having a working surface of 434 mm² on groups of coils which have been used in the cracking furnace for about the same time. Further measurements were conducted on coils which had been replaced from such furnace.

TABLE 3

Static attractive force measurement of 376 coils* in a cracking furnace heated from the side and a ruptured coil used in such cracking furnace

| Coil ID number | Age at time of measure | Measured force (N) | Measured force per area (mPa) |
|---|---|---|---|
| No. 1 to 144 | 8.5 years | <1 | <2.3 |
| No. 145 to 197 | 2.83 years | <1 | <2.3 |
| No. 198** | 2.83 years | 19 | 43.7 |
| No. 199 | 2.83 years | <1 | <2.3 |

TABLE 3-continued

Static attractive force measurement of 376 coils*
in a cracking furnace heated from the side and
a ruptured coil used in such cracking furnace

| Coil ID number | Age at time of measure | Measured force (N) | Measured force per area (mPa) |
|---|---|---|---|
| No. 200-202** | 2.83 years | 17-21 | 39.1-48.3 |
| No. 203 | 2.83 years | 11 | 25.3 |
| No. 233 to 376 | 8.75 years | <1-5 | <2.3-11.5 |
| Ruptured coil | age at time of rupture: 7 years + 3 month | 57 | 131.1 |

*coils were made of either GX45NiCrSiNbTi25-25, GX55CrNiSiNbTi30-30, GX45NiCrSiNbTi45-35 or GX10NiCrNb32-20
**coils were decommissioned and replaced in light of measurement Comparative Measurements of Adhesive Versus Attractive Force:

A series of measurements were performed on an approximately 325 mm long portion of two decommissioned coils, where adhesive and static attractive measurements were made at six positions along the length of the tube at 50 mm intervals starting from one end of the coil segment and dynamic attractive force measurements were made over a length of 250 mm starting from the first position and ending at the sixth position, utilizing different velocities by which the magnet was moved over the surface of the coils. The results of the measurements are provided in the following Tables 4 and 5.

TABLE 4

Adhesive and attractive force measurements of a portion of a damaged and decommissioned coil originally made of GX45NiCrSiNbTi35-25 and having an age of six years at the time of replacement

| Position | Distance from one end | Measured adhesive force (N) | Measured static attractive force (N) | Measured dynamic attractive force* (N) from $1^{st}$ to $6^{th}$ position | | |
|---|---|---|---|---|---|---|
| | | | | @ 50 mm/s | @ 100 mm/s | @ 200 mm/s |
| 1. | 50 | 16.2 | 16.1 | 18.2 | 18.1 | 17.6 |
| 2. | 100 | 15.9 | 16.1 | | | |
| 3. | 150 | 16.3 | 15.9 | | | |
| 4. | 200 | 14.6 | 14.8 | | | |
| 5. | 250 | 17.3 | 17.1 | | | |
| 6. | 300 | 18.3 | 18.1 | | | |

*the maximal force value observed over the measured length is reported.

TABLE 5

Adhesive and attractive force measurements of a portion of a damaged and decommissioned coil originally made of GX10NiCrNb32-20 and having an age of three years at the time of replacement*

| Position | Distance from one end | Measured adhesive force (N) | Measured static attractive force (N) | Measured dynamic attractive force** from $1^{st}$ to $6^{th}$ position (N) | | |
|---|---|---|---|---|---|---|
| | | | | @ 50 mm/s | @ 100 mm/s | @ 200 mm/s |
| 1. | 50 | 18.3 | 17.6 | 22.3 | 22.2 | 21.9 |
| 2. | 100 | 18.2 | 18.1 | | | |
| 3. | 150 | 22.5 | 22.1 | | | |
| 4. | 200 | 20.4 | 20.5 | | | |
| 5. | 250 | 18.3 | 18.4 | | | |
| 6. | 300 | 19.2 | 19.1 | | | |

*a portion of one of the measured coils from Table 3, in particular a portion of the coil No. 198.
**the maximal force value observed over the measured length is reported.

What is claimed is:

1. A method of detecting carburization, nitriding or chromium depletion in a non- or weakly ferromagnetic coil, comprising the steps:
    a) applying a permanent magnet having a magnet pull force equal to or greater than about 75 N to a surface of the non- or weakly ferromagnetic coil; and
    b) measuring the adhesive force to detach the magnet from the coil.

2. The method according to claim 1, wherein the coil is a conduit comprising austenitic stainless steel.

3. The method of claim 1, wherein the coil is a furnace coil, a part of furnace coil, cracking coil, or part of a cracking coil.

4. The method of to claim 1, wherein the surface of the magnet facing towards the surface of the coil is the working surface of the magnet, the step of measuring the adhesive force further includes applying a gradually increasing force such that the magnet is being pulled away from the surface of the coil, and the adhesive force is being applied in a direction perpendicular to the working surface of the magnet and through the center of force of the magnet and continuing application of the adhesive force until the magnet detaches from the surface of the coil.

5. The method of claim 1, wherein in the step of applying, the working surface of the magnet is placed directly in contact with the surface of the coil or the working surface is placed in indirect contact with the surface of the coil via one or more non-magnetic spacers having a known or specified thickness, said one or more spacers being located between the working surface of the magnet and the surface of the coil.

6. A method of detecting carburization, nitriding or chromium depletion in a non- or weakly ferromagnetic coil, comprising the steps:
   a) positioning a permanent magnet having a magnet pull force equal to or greater than about 75 N at a fixed distance from a surface of a non- or weakly ferromagnetic coil, having a working surface defined as the surface of the magnet facing towards the surface of the coil and which working surface is not in direct or indirect contact with the surface of the coil; and
   b) measuring the attractive force in which the magnet is being pulled towards the surface of the coil.

7. The method of claim 6, wherein the fixed distance between the working surface of the magnet and the surface of the coil is in the range from about 0.05 mm to about 6 mm.

8. The method of claim 6, wherein in the step of measuring, the attractive force is being measured in a direction perpendicular to the working surface of the magnet and through the center of force of the magnet.

9. The method of claim 6, wherein the magnet is displaced over the surface of the coil while maintaining the fixed distance and measuring the attractive force.

10. The method of claim 6, wherein the magnet is attached to a hand-held electronic force measurement device via a bracket which includes wheels or rollers.

11. The method of claim 1, wherein the magnet has a magnet pull force equal to or greater than about 90 N.

12. The method of claim 1, wherein the magnet is a rare earth magnet.

13. The method of claim 1, wherein when the magnet is placed against the surface of the coil, the magnet can make contact over the complete surface area of its working surface to the surface of the coil being measured.

14. A method of monitoring the conditions of coils for cracking hydrocarbons in a furnace, comprising the steps:
   a) applying a permanent magnet having a magnet pull force equal to or greater than about 75 N to a surface of the coils located in situ in a furnace; and
   b) repeatedly measuring the adhesive force to detach the magnet from the coils.

15. The method of claim 1, wherein the magnet has a magnet pull force equal to or less than about 750 N.

16. The method of claim 1, wherein when the magnet is placed against the surface of the coil, (a) the magnet can make contact over a portion of the surface area of its working surface to the surface of the coil being measured and (b) the remaining portion of the surface area of the magnet working surface remains spaced apart from the surface of the coil at a distance of no greater than about 1.5 mm.

* * * * *